(12) United States Patent
Evans et al.

(10) Patent No.: US 9,072,847 B2
(45) Date of Patent: Jul. 7, 2015

(54) APPARATUS AND METHOD OF FLUID DELIVERY

(75) Inventors: Nicholas Evans, South Brent (GB); Kenneth Smith, South Brent (GB)

(73) Assignee: SurgicalEdge Systems Limited (GB)

( * ) Notice: Subject to any disclaimer, the term of this patent is extended or adjusted under 35 U.S.C. 154(b) by 852 days.

(21) Appl. No.: 13/129,783

(22) PCT Filed: Nov. 19, 2009

(86) PCT No.: PCT/GB2009/051569
§ 371 (c)(1),
(2), (4) Date: Jul. 13, 2011

(87) PCT Pub. No.: WO2010/058216
PCT Pub. Date: May 7, 2010

(65) Prior Publication Data
US 2011/0282273 A1   Nov. 17, 2011

(30) Foreign Application Priority Data

Nov. 20, 2008   (GB) .................................. 0821180.7

(51) Int. Cl.
*A61M 13/00* (2006.01)
*A61F 9/007* (2006.01)

(52) U.S. Cl.
CPC .......... *A61M 13/003* (2013.01); *A61F 9/00736* (2013.01); *A61M 2205/3344* (2013.01); *A61M 2205/3355* (2013.01); *A61M 2210/0612* (2013.01)

(58) Field of Classification Search
CPC .............. A61M 13/00; A61M 13/003; A61M 2202/0208; A61M 2202/0225; A61M 2202/0233; A61M 2205/3344; A61M 2205/3355; A61M 2210/0612; A61F 9/00736
USPC ...................................................... 604/23–26
See application file for complete search history.

(56) References Cited

U.S. PATENT DOCUMENTS

| | | | |
|---|---|---|---|
| 2,812,716 A | 11/1957 | Gray | |
| 3,353,537 A | 11/1967 | Knox et al. | |
| 4,324,243 A | 4/1982 | Helfgott et al. | |
| 4,909,783 A | 3/1990 | Morrison | |
| 5,176,645 A | 1/1993 | Guerrero | |
| 5,261,883 A * | 11/1993 | Hood et al. | 604/153 |
| 5,715,824 A * | 2/1998 | Unger et al. | 424/9.51 |
| 6,068,640 A | 5/2000 | Gordon et al. | |
| 6,290,690 B1 | 9/2001 | Huculak et al. | |
| 7,533,669 B2 * | 5/2009 | Fuhrman et al. | 128/203.25 |
| 2002/0019607 A1 | 2/2002 | Bui | |
| 2007/0073234 A1 | 3/2007 | Nazarifar et al. | |

OTHER PUBLICATIONS

PCT International Search Report for International Application No. PCT/GB2009/051569 dated Jul. 29, 2010.

(Continued)

*Primary Examiner* — Theodore Stigell
(74) *Attorney, Agent, or Firm* — Winstead, P.C.

(57) ABSTRACT

Apparatus for gas delivery (10), particularly at low pressure and volume. The apparatus has a gas reservoir, a delivery line between the gas reservoir (14) and a gas outlet (68) and a first supply line between a first inlet connect able to a first gas supply and the gas reservoir. A pressure control line is provided with an inlet connect able to a second gas supply. The pressure control line is coupled to the gas reservoir to thereby control the pressure in the gas reservoir.

20 Claims, 1 Drawing Sheet

(56) References Cited

OTHER PUBLICATIONS

Search Report for Great Britain Application No. GB0821180.7 from United Kingdom Patent Office dated Feb. 24, 2009.

Search Report for Great Britain Application No. GB0920215.1 from United Kingdom Patent Office dated Mar. 17, 2010.

* cited by examiner

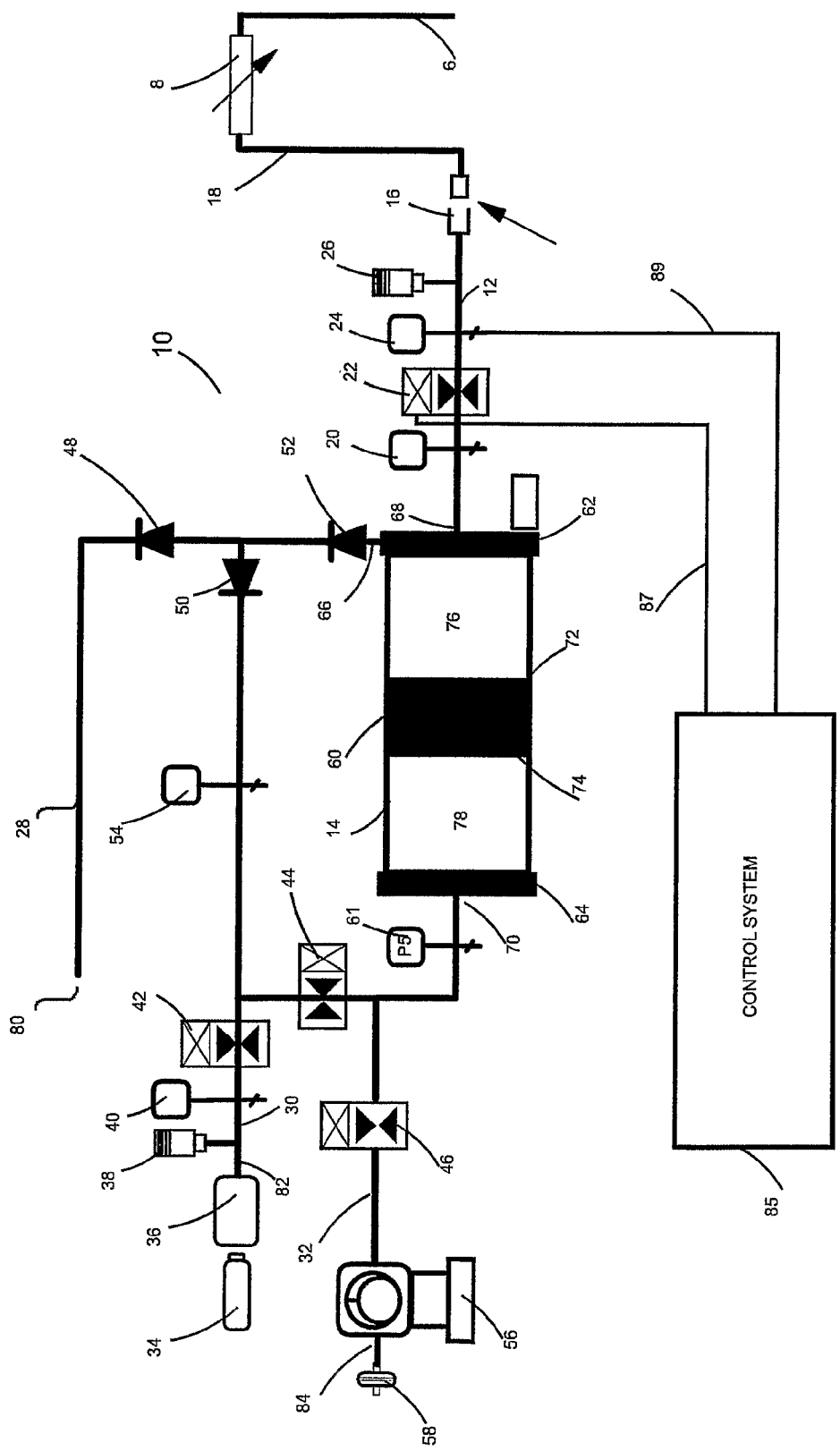

APPARATUS AND METHOD OF FLUID DELIVERY

CROSS REFERENCES TO RELATED APPLICATIONS

The present application is a continuation-in-part application of and is a U.S. National Stage Application under 35 U.S.C. §371 of International Application No. PCT/GB2009/051569, filed on Nov. 19, 2009, which claims the benefit of Great Britain Patent Application No. 0821180.7, filed Nov. 20, 2008; the complete disclosures of which are incorporated herein by reference.

The present invention relates to an apparatus and method for fluid delivery, in particular delivery of gas at low pressure and low volume. The apparatus and method are particularly suitable for delivering custom mixed fluids.

One particular field in which low pressure and low volume of gas delivery is required is eye surgery, for example vitreo-retinal surgery.

Vitreo-retinal surgery is used, inter alia, to repair retinal detachment, to remove intra-ocular foreign bodies, to treat infections and injuries to the inner eye and generally to manipulate the retina. Both internal and external surgical approaches can be employed, according to the specific clinical indications. During surgery, it may be necessary to inject fluids to supplement or replace the vitreous humour, in order to maintain an appropriate internal pressure or to close retinal breaks. Such fluids may either be liquid (for example silicone oil) or gaseous (for example air, sulphur hexafluoride ($SF_6$), perfluoroethane ($C_2F_6$), perfluoropropane ($C_3F_8$ or a mixture of two or more such gases).

The longer a fluid is intended to be retained in the eye, the greater the need for it to be a fluid other than water or air, which is less likely to be absorbed, hence the need in such situations for gases of low solubility, or for liquids such as silicone oils. As a result, intra-ocular silicone oil may be used either as a temporary or as a permanent filler to maintain eye pressure, whilst intra-ocular gases tend to be used only temporarily, the duration of use being dependent on the solubility of the relevant fluid.

In some types of ocular surgery, in particular vitrectomy, the vitreous humour (which is the natural gel in the posterior segment of the eye) may be removed. During this procedure the intra-ocular pressure and volume are preferably maintained by continuous infusion of a suitable fluid, of the type described above. Following the surgery, again a suitable fluid may be used to replace the infusion fluid, there being in this case a need for a less soluble fluid which will not be reabsorbed too quickly. Thus a relatively low solubility but biocompatible gas such as sulphur hexafluoride, perfluoroethane or perfluoropropane may be utilised for this purpose.

When introducing a fluid into the eye it is important that the intra-ocular pressure be maintained within physiological limits throughout the entire procedure. With this in mind it is desirable that the delivery pressure and flow rate of the fluid can be accurately controlled.

If a mixture of fluids is to be introduced, there is also a need to control the ratio of each of the components of the mixture as well as the volume rate delivery and the resultant intra-ocular pressure.

The introduction of a fluid into the eye requires careful and experienced clinical judgement regarding the appropriate type and concentration of fluid, and the pressure and flow rate of its delivery. Currently fluids tend to be introduced and/or mixed manually using a syringe, with only finger pressure to gauge the flow rate and the intra-ocular pressure. As with any manual operation there is considerable scope for human error during such a procedure.

A first aspect of the present invention provides apparatus for fluid delivery, comprising:
 a fluid reservoir;
 a delivery line between the fluid reservoir and a fluid outlet;
 a first supply line between a first inlet connectable to a first fluid supply and the fluid reservoir;
 a pressure control line with an inlet connectable to a second fluid supply, the pressure control line being coupled to the fluid reservoir to thereby control the pressure in the fluid reservoir.

The invention provides automated delivery of fluid and is suitable for automated delivery of fluid to an eye.

Flow of fluid through the pressure control line may be used to maintain adequate pressure in the fluid reservoir during delivery of fluid from the fluid outlet, for example to an eye.

The fluid may comprise a gas, preferably a biocompatible gas.

The delivery line and first supply lines may comprise separate lines.

In one embodiment, a first supply line and delivery line are connected to a first region of the reservoir, enabling fluid to be delivered into and extracted from the fluid reservoir and wherein the pressure control line is connected to a second region of the reservoir, enabling control of the pressure within the first region.

The fluid reservoir may comprise a cylindrical chamber and a piston. The cylindrical chamber may have a first region defined by a first end of the chamber and a first face of the piston, wherein the first region is provided with an inlet coupled to the first supply line and an outlet coupled to the delivery line The cylindrical chamber may have a second region defined by a second end of the chamber and a second face of the piston, wherein the second region is provided with an opening coupled to said pressure control line.

The interface between the piston and the inner surface of the cylindrical chamber may be gas tight, permitting leakage at the rate of less than 0.1 $cm^3$/hour at applied pressure 2 bar (200 kPa). The interface between the piston and the inner surface of the cylindrical chamber may be low friction permitting free movement in either direction of travel at applied pressure 0.005 bar (0.5 kPa) For example, the inner surface of the cylindrical chamber may comprise glass and the outer surface of the piston may comprise ground glass. Materials other than glass may also be suitable.

In an embodiment, the apparatus comprises a second supply line connecting the second fluid supply and one of the fluid reservoir and delivery line. It may also comprise a third supply line connecting a third fluid supply and one of the reservoir and delivery line. In one embodiment, the apparatus comprises a second supply line connecting the second fluid supply and the fluid reservoir and a third supply line connecting a third fluid supply and the fluid reservoir.

The working pressure of the fluid reservoir may be higher than the pressure in the delivery line.

The delivery line may have a variable flow rate. Feedback of the pressure at the outlet may be used to control the flow rate through the delivery line.

The apparatus may be provided with a control system, for example a processor, such as a micro-processor or personal computer (PC). The control system may receive data from one or more pressure sensors in the apparatus. The control system may receive data from one or more valves in the apparatus. The control system may generate one or more outputs to control one or more valves in the apparatus. Feedback of the pressure at the outlet to control the flow rate through the delivery line may be generated in the control system. The feedback may be generated using data from at least one pressure sensor at the outlet.

In one embodiment, the delivery line is provided with a valve to control the pressure at the outlet. The valve may comprise a proportional valve. The working pressure of the valve in the delivery line may be less than 100 mm Hg (13.3 kPa). The working pressure of the valve in the delivery line may be less than 50 mm Hg (6.7 kPa). The flow rate may be between 0 cm$^3$/minute and 100 cm$^3$/minute In one embodiment, the working pressure of the fluid reservoir is less than 200 mm Hg (26.7 kPa). The volume of the fluid reservoir may be about 50 cm$^3$.

In an embodiment, the fluid reservoir has a fixed mode in which the piston is located at one end to form a conduit between the first supply line and the delivery line.

The fluid reservoir may include a sensor to measure the volume of gas in the fluid reservoir, for example this may comprise a position sensor to measure the position of the piston in the fluid reservoir.

The second fluid supply may be an air supply. The supply may comprise an air pump. The air pump may comprise a variable speed air pump. The first inlet may be configured to receive a syringe. The third inlet may be configured to receive a gas cylinder, for example a micro cylinder.

Valves may be provided for selection between the different lines.

The delivery line may further comprise a pressure sensor and feedback from the pressure sensor may control the valve, to thereby deliver fluid at constant pressure. The delivery line may further comprise two pressure sensors, one on either side of the valve and wherein the two pressure sensors are used to determine the flow rate across the valve. The two pressure sensors may provide feedback to control the valve. The delivery line may comprise a safety relief valve to prevent pressure exceeding a threshold value, for example 50 mmHg (6.7 kPa). The data from pressure sensors may be output to a control system, which may calculate flow rate across a valve and/or generate feedback to control a valve.

In one embodiment, the apparatus comprises a low pressure override mode, which prevents the pressure in at least one of the delivery line, supply line or fluid reservoir dropping below a threshold value. In the low pressure override mode, the second fluid supply may be a default fluid supply if the pressure of at least one of the delivery line, supply line or fluid reservoir drops below a predetermined threshold.

A second aspect of the invention provides apparatus for delivering a fluid to a patient's body.

The apparatus may further comprise a medical device suitable for injecting a fluid from the fluid delivery apparatus to a patient's body.

The apparatus may be suitable for delivering a fluid to a patient's eye.

A third aspect of the present invention provides a method of delivering fluid comprising:
  selecting a fluid from at least a first fluid supply and a second fluid supply;
  inputting said fluid into a fluid reservoir;
  using the second fluid supply to maintain the fluid reservoir at a working pressure;
  outputting the fluid from the fluid reservoir through a delivery line, the delivery line having a lower pressure than the working pressure.

A fourth aspect of the present invention provides a method of delivering gas comprising:
  inputting a gas into a fluid reservoir;
  using a second gas supply to maintain the fluid reservoir at a working pressure;
  outputting the gas from the fluid reservoir through a delivery line, the delivery line having a lower pressure than the working pressure.

The method may comprise the step of adjusting the flow rate of the fluid through the delivery line to maintain constant pressure at the outlet of the delivery line. The method may further comprise the step of monitoring the pressure at the outlet of the delivery line and using feedback from the pressure to adjust the flow rate.

The method may comprise the step of selecting a gas to be inputted into the fluid reservoir from a first gas supply and the second gas supply.

In one embodiment, the step of inputting a gas into a fluid reservoir comprising inputting a gas mixture. This may comprise the step of inputting a known volume of a first gas and inputting a known volume of a second gas.

A fifth aspect of the present invention provides a method for measuring the flow rate of a fluid, the method involving:
  passing the fluid from the a first fluid supply through the apparatus outlined according to any of the first or second aspects of the invention,
  using fluid from a second fluid supply to maintain a working pressure within the apparatus.

A sixth aspect of the present invention provides a method for delivering a fluid to a device through which the fluid is intended to be introduced into a body, in particular an eye, the method involving passing the fluid through the apparatus.

A seventh aspect of the present invention provides apparatus for fluid delivery, comprising:
  a fluid reservoir formed from a cylindrical chamber and piston, containing a first region on one side of the piston and a second region on the second side of the piston;
  a delivery line between the first region of the fluid reservoir and a fluid outlet;
  a first supply line between a first inlet connectable to a first fluid supply and the first region of the fluid reservoir;
  a second supply line between a second inlet connectable to a second fluid supply and the first region of the fluid reservoir or the delivery line;
  a pressure control line coupling the second fluid supply and a second region of the fluid reservoir, to thereby control the pressure of the first region.

An eighth aspect of the present invention provides apparatus for fluid delivery, comprising:
  a fluid reservoir;
  a delivery line between the fluid reservoir and a fluid outlet;
  a first supply line between a first inlet connectable to a first fluid supply and the fluid reservoir;
  a second supply line between a second inlet connectable to the second fluid supply and the fluid reservoir;
  a third supply line between a third inlet connectable to a third fluid supply and the fluid reservoir;
  a pressure control line connectable to the second fluid supply, the pressure control line being coupled to the fluid reservoir to thereby control the pressure in the fluid reservoir.

A ninth aspect of the invention comprises a method of delivering gas comprising:
  inputting a known volume of a first gas into a gas reservoir;
  inputting a known volume of a second gas into the gas reservoir;
  outputting the mixed gas from the gas reservoir through a delivery line;
  wherein the known volume of the first gas and known volume of the second gas are input into the gas reservoir in incremental sub stages.

The incremental sub stages may comprise alternately inputting a fraction of the known volume of the first gas and a fraction of the known volume of the second gas.

This method of mixing gas is suitable for mixing gases of substantially different densities. For example, the first gas may comprise air and the second gas may be selected from the group comprising sulphur hexafluoride ($SF_6$), perfluoroethane ($C_2F_6$), perfluoropropane ($C_3F_8$).

The pressure within the gas reservoir may be controlled by a variety of means. For example, the gas reservoir may comprise a chamber and piston, wherein the piston is controlled by any means, for example hydraulics, electric motor, pneumatically etc.

Preferred features of the second, third, fourth, fifth, sixth, seventh, eighth and ninth aspects of the invention may be as described above in connection with the first aspect.

Throughout the description and claims of this specification, the words "comprise" and "contain" and variations of the words, for example "comprising" and "comprises", mean "including but not limited to", and do not exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Other features of the present invention will become apparent from the following example. Generally speaking the invention extends to any novel one, or any novel combination, of the features disclosed in this specification (including any accompanying claims and drawings). Thus features, integers, characteristics, compounds, chemical moieties or groups described in conjunction with a particular aspect, embodiment or example of the invention are to be understood to be applicable to any other aspect, embodiment or example described herein unless incompatible therewith.

Moreover unless stated otherwise, any feature disclosed herein may be replaced by an alternative feature serving the same or a similar purpose.

The present invention will now be described by way of example only and with reference to the accompanying illustrative drawings:

FIG. 1 illustrates a schematic layout of the fluid delivery apparatus of the present invention.

FIG. 1 illustrates an apparatus 10 for delivering low volumes of gas at low pressure to an eye during a surgical procedure. The pressures used are typically within an operating range of about 10-100 mm Hg (1.3-13.3 kPa), with an optimum of about 30 mm Hg (4.0 kPa), although the pressure may be as low as 1 mm Hg (0.1 kPa). A typical operation would require 10 $cm^3$ of gas; however more will be required for purging.

The eye 8 is represented as a variable resistor in FIG. 1, to illustrate its variable internal pressure. During a surgical procedure, a cannula 18 is inserted into the eye for delivering fluid and a drain 6 may optionally also be inserted.

It is desirable to maintain the eye at constant pressure. However as the eye has a variable leak characteristic, a variable flow rate of fluid is required to be delivered to the eye to keep it at constant pressure.

As shown in FIG. 1, delivery line 12 is used to deliver the chosen gas to the eye. Line 12 is connected to fluid reservoir 14 at one end and connection point 16 at the other. The cannula 18 for insertion into the eye can be connected to the connection point 16.

As will be described in more detail, the fluid reservoir 14 contains a chosen pure gas or gas mix for delivery to the eye. The gas within the fluid reservoir is kept at a 'working pressure' for example 200 mm Hg (26.7 kPa).

Between the fluid reservoir 14 and the connection point 16, delivery line 12 is provided with a pressure sensor 20, valve 22, pressure sensor 24 and pressure relief valve 26.

The relief valve 26 provides a safety system to prevent the eye being exposed to pressure in excess of a threshold. The threshold is set to a pressure that the eye can withstand for small periods of time, for example 50 mm Hg (6.7 kPa). This ensures that the pressure of gas delivered to the eye cannot exceed this pressure, even if there is a malfunction in the system.

The valve 22 controls the flow rate and therefore the pressure of gas which will be delivered to the eye via the cannula 18. The valve 22 is a proportional valve, in which the operation of the valve is proportional to voltage applied. Proportion valves are very sensitive, with a typical turn down value of 100:1, which provides good control.

The pressure of the eye is sensed by pressure sensor 24, whilst pressure sensor 20 senses the pressure of the gas in the fluid reservoir. The two pressure sensors 20,24 on either side of the valve 22 measure the flow rate across it.

The apparatus includes control system 85, typically comprising a micro-processer or alternatively a PC. The control system receives input signals from the pressure sensors and valves and outputs signals to control the valves. FIG. 1 shows only the signal lines between the pressure sensor 24 and the valve 22 and the control system 85 for clarity.

The required intra-ocular pressure is determined on a case by case basis, depending for example on the procedure to be carried out and the condition of the eye. As pressure sensor 24 measures the actual pressure in the eye, the difference between the actual pressure and the desired pressure can be used as feedback to control valve 22. Thus valve 22 can be adjusted so that it provides the required flow rate to deliver the desired pressure of gas. The feedback calculation occurs in the control system 85.

The gas may be delivered to the eye in two modes. The eye may be provided with both a cannula for supplying the gas and a drain. In this case, the eye should be kept at a constant pressure and pressure sensor 24 is used to monitor the pressure and provide feedback to valve 22 to adapt the flow rate to maintain the pressure. Alternatively, the eye may be a closed system, without a drain, in which case the flow rate will be very low, reaching zero when the terminal pressure is achieved. This requires a 'terminal pressure mode' in which the flow rate is adjusted to maintain and achieve a desired pressure. As before, the pressure sensor 24 is used to monitor the pressure in the eye. The pressure values measured by pressure sensors 20 and 24 on either side of valve 22 are used to determine the flow rate through the valve 22. Feedback from these pressure sensors 20,24 is used to control the valve 22 to achieve the required flow rate to achieve and maintain the terminal pressure. The closed eye typically has a pressure of 30 mm Hg (4.0 kPa) and a suitable typical flow rate would be in the region of 0.5 $cm^3$/min.

The fluid reservoir 14 is a cylindrical chamber containing a piston 60. The cylindrical chamber has a first end 62 which contains a gas inlet 66 through which gas from any of lines 28,30,32 is introduced. The first end also contains a gas outlet 68, through which gas in the fluid reservoir 14 is expelled into delivery line 12.

The cylindrical chamber has a second end 64, opposite to the first end 62. The second end is provided with an aperture 70. The aperture connects to pipework which communicates with lines 30 and 32.

A first region 76 of the fluid reservoir is defined between the first end of the cylindrical chamber and a first face 72 of the piston. Gas to be delivered through delivery line 12 is stored in this region. A second region 78 is defined between the second face 74 of the piston and the second end 64 of the cylindrical chamber. This region is used to control the pressure of the gas within the first region.

The interface between the piston and cylindrical chamber has low friction and is gas tight; both these parameters are required for accuracy. The cylindrical chamber and piston are both made of glass, the surface of the piston being ground glass. These materials produce the desired low friction, gas tight interface; however other materials may be used.

To have sufficiently low friction, the piston must be able to fall under its own weight due to gravity, when the cylinder is angled at 30-40°. To be sufficiently gas tight, if one end of the cylinder is blocked, and the piston pressurised with a 2 kg load, there is no appreciable movement of the piston in one week.

A position sensor (not shown) is provided on the piston and cylinder to measure the volume of gas in the cylindrical chamber.

The apparatus is able to deliver gases from different sources. The gas may be stored in a sealed container for example a gas cylinder, be air from the atmosphere or be a custom mix, for example prepared in a syringe.

The apparatus has three input lines 28,30,32, one for each type of gas supply. These three input lines and their modes of operation are described below.

The three input lines 28,30,32 each extend from a gas input end 80,82,84 to an input in the fluid reservoir 14. FIG. 1 shows one configuration of pipework but others are possible. As can be seen from FIG. 1, some of the input lines may have shared pipework.

Valves 42,44,46 and one way valves 48,50,52 are provided to control the flow of gas from each gas source to the fluid reservoir 14. Valves 44,46 are on/off valves and valve 42 is a proportional valve, which enables sections of the different lines to be opened or closed, thereby enabling the selection of the input line for the chosen gas supply.

Gas supplied in a pre-filled container, for example a gas cylinder is delivered using delivery line 30. The gas cylinder may be filled with a pure gas, such as $SF_6$, $C_3F_8$ or $C_2F_6$ or a pre-defined gas mixture, e.g. 20% $SF_6$:air mix. The cylinder is typically provided full by a gas supplier and has a bar code which identifies the gas or mixture of gases contained therein, in addition to the percentage mix and pressure.

The gas cylinder 34 is typically a micro cylinder of 100 psi (689.4 kPa) pressure. A micro cylinder typically contains 50 $cm^3$ of working volume of gas (i.e. 50 $cm^3$ at atmospheric pressure). For delivery of low volumes of gas (such as a pure, undiluted gas), only about 2 $cm^3$ will be required. Micro cylinders are single use capsules and are not refilled.

The cylinder 34 is inserted into the apparatus by screwing it into chamber 36.

To enable delivery of gas from the cylinder 34, valve 42 is opened, whilst valves 44 and 46 are closed. Thus gas from cylinder 34 flows through line 30, via valve 42, one-way valves 50,52 and into the fluid reservoir 14.

As the gas flows from the micro cylinder 34 through line 30, it passes through a pressure relief valve 38, and two pressure sensors 40,54. The pressure relief valve 38 is provided to release excess pressure, for example over a threshold of 180 psi (12 bar). Pressure sensor 40 detects the pressure of the gas within the micro cylinder 34 and produces a low gas warning when the pressure drops below a certain threshold.

Valve 42 is a proportional valve and can be used to adjust the working pressure of gas, which is kept constant at 200 mm Hg (26.7 kPa). After passing through valve 42, the gas passes through pressure sensor 54. As in line 12, feedback from pressure sensor 54 is used to control valve 42. In this way a constant working pressure is maintained.

If the gas supply is air, line 32 is used. The air is supplied from the atmosphere via a pump 56. The pump is a variable speed pump, enabling the pressure and flow rate to be varied. As the air is supplied from the atmosphere, there is no risk of the air supply running out. A filter 58 is supplied at the air inlet of the pump to filter the air. Two pumps (or more) may be provided, as a failsafe provision.

In order for air to be delivered through line 32, valves 46 and 44 are opened whilst valve 42 is closed. This enables the air to flow through line 32 via valves 46,44 and one-way valves 50,52 and into the fluid reservoir 14.

If the gas supply is a custom supply, it is delivered through line 28. In this case, a gas mixture is typically prepared in a syringe and injected into line 28. When a custom gas mix is used, the gas flows through line 28 via one way valves 48,52 to the fluid reservoir.

Alternatively, the fluid reservoir itself may be used to prepare the custom gas mix.

When the gas source is either a pre-filled container or air, the piston 60 may be moved so that its first face 72 is adjacent the first end 68 of the cylindrical chamber. When the piston is in this position, a conduit is formed between the inlet 66 and outlet 68, through which the gas flows. In this case, the 'working pressure' of the gas is controlled for the pre-filled container by proportional valve 42 (with feedback from pressure sensor 54) and for the air source by the speed of the pump 56 (again with feedback from pressure sensor 54).

When a custom mix of gas is used, the mode of operation is slightly different. The air pump 56 is turned off and any micro cylinders 34 attached to line 30 are removed. Valve 46 is closed and valves 42,44 are opened. The custom gas mixture is injected into line 28 and flows via one-way valves 48,52 into the fluid reservoir via inlet 66. As the gas enters the cylindrical chamber, it displaces the piston 60 towards the second end 64. As the piston 60 moves, air within the cylindrical chamber between the second face 74 of the piston and the second end 64 of the cylindrical chamber is expelled through the aperture 70 and flows via valves 44,42 to exit from the input of line 30. As valves 42,44 are open, the piston gives very little resistance against the custom mix of gas entering the cylindrical chamber.

Alternatively the fluid reservoir itself can be used to prepare the gas mixture. In this case pump 56 is put in reverse flow to aspirate the reservoir. A first gas is then introduced into the fluid reservoir, using a position sensor to measure the volume in the reservoir. A second gas is then introduced into the fluid reservoir to the desired volume. Both gases can be supplied via the supply lines describe above. The advantage of using the fluid reservoir to measure out and mix the gases is that it enables the process to be automated and removes human error.

A typical gas mix for use in eye surgery is 20% gas (e.g. $SF_6$) and 80% air. As $SF_6$ and other gases used in eye surgery have significantly higher density than air, it can be difficult to obtain a homogeneous mix. In the present invention, a homogeneous mix can be obtained by mixing the gas and air in successive part-stages. In a 50 $cm^3$ reservoir, a 20% gas mix can be achieved by drawing in 10 $cm^3$ gas followed by 40 $cm^3$ air. However, an improved homogeneous gas mix can be achieved by drawing in the gas and air in incremental substages, for example 5 cm$^3$ gas/20 cm$^3$ air then 5 cm$^3$ gas/20 cm$^3$ air; or 1 cm$^3$ gas then 4 cm$^3$ air, 1 cm$^3$ gas/4 cm$^3$ air, etc up to 50 cm$^3$). The appropriate mixing can be achieved by an appropriate routine in the controlling software.

When the custom gas mixture is within the fluid reservoir, valves 42,44 are closed and valve 46 is opened. Line 32 containing the air pump 56 is now in communication with the second region 78 of the cylindrical chamber between the second face 74 of the piston and the second end 64 of the cylindrical chamber, via the aperture 70. The air pump 56 is used to pump air through aperture 70 and into the second region 78 of the cylindrical chamber. The air within the second region 78 of the cylindrical chamber generates a pressure against the piston 60, which is measured by pressure sensor 61. Feedback from the pressure sensor 61 is used to control the air pump 56 and maintain a working pressure within the fluid reservoir, for example of 200 mm Hg (26.7 kPa).

The air pressure exerted on the piston causes the piston to exert a pressure on the custom gas mix within the chamber, thereby creating the required working pressure of the custom gas.

Valve 46 is optional and is not required if the speed/pressure of the air pump is variable.

Use of air to actuate the piston has the advantage that it uses the pre-existing air supply, thus simplifying the system and removing the need for more complicated mechanical actuators, for example lead screws etc to actuate the piston. Furthermore as atmospheric air is used, there is no risk of it running out.

The air supply is also used as a safety system; in addition to protecting the eye from excess pressure, it must also be protected from the pressure dropping too low. As the supply of air is unlimited, it can be used as an override if the pressure of either the gas from the micro cylinder or the custom mix becomes too low, for example by running out of gas. In this case, valves 44,46 are opened and valve 42 closed, to deliver air from the air pump 56 to the delivery line.

Whilst the above description describes different modes of use for the fluid reservoir depending on the source of gas, gas from both the air supply and micro cylinder can be delivered using the fluid reservoir in the same manner as described with reference to custom mixed gases. Additionally, the pipework layout could be adjusted so that the gas supplied from either or both of the air supply and micro cylinder are not input into the fluid reservoir but instead join the delivery line 12 directly, in this case between fluid reservoir 14 and pressure sensor 20.

The extremely low flows and pressures handled by this apparatus makes it particularly suitable for maintaining intraocular pressure during eye surgery. However, the apparatus is also applicable for industrial uses.

The invention claimed is:

1. Apparatus for gas delivery, comprising:
   a gas reservoir comprising a cylindrical chamber and a piston, the cylindrical chamber comprising a first region defined by a first end of the chamber and a first face of the piston and a second region defined by a second end of the chamber and a second face of the piston;
   a delivery line between the first region of the gas reservoir and a gas outlet, the delivery line being provided with a valve to control pressure at the gas outlet;
   a first supply line between a first inlet connectable to a first gas supply and the first region of the gas reservoir;
   a pressure control line with an inlet connectable to a second gas supply, the pressure control line being coupled to the second region of the gas reservoir to thereby maintain a working pressure in the first region of the gas reservoir, said working pressure being higher than the pressure in the delivery line.

2. Apparatus according to claim 1 wherein the inner surface of the cylindrical chamber comprises glass and the outer surface of the piston comprises ground glass.

3. Apparatus according to claim 1 further comprising a second supply line connecting a second fluid supply and one of the gas reservoir and delivery line.

4. Apparatus according to claim 3 further comprising a third supply line connecting a third gas supply and one of the gas reservoir and delivery line.

5. Apparatus according to claim 1 wherein the delivery line is provided with a valve to control the flow rate at the outlet.

6. Apparatus according to claim 5 wherein the working pressure of the valve in the delivery line is less than 50 mm Hg.

7. Apparatus according to claim 1 wherein the flow rate at the outlet is between 0 cm$^3$/minute and 100 cm$^3$/minute.

8. Apparatus according to claim 1 wherein the working pressure of the gas reservoir is less than 200 mm Hg.

9. Apparatus according to claim 1 wherein the gas reservoir has a fixed mode in which the piston is located at one end to form a conduit between the first supply line and the delivery line.

10. Apparatus according to claim 1 wherein the second gas supply is an air supply.

11. Apparatus according to claim 1 wherein the first inlet is configured to receive a syringe.

12. Apparatus according to claim 4 wherein the third supply line is configured to receive a gas cylinder.

13. Apparatus according to claim 1 further comprising a second supply line connecting a second fluid supply and one of the gas reservoir and delivery line, a third supply line connecting a third gas supply and one of the gas reservoir and delivery line and a valves for selection between the first, second and third supply lines.

14. Apparatus according to claim 1 further comprising a control system which receives data from one or more pressure sensors in the apparatus, wherein the control system has a low pressure override mode, which prevents the pressure in at least one of the delivery line, supply line or gas reservoir dropping below a threshold value.

15. Apparatus according to claim 1, further comprising:
   a pressure sensor for measuring the pressure within the second region of the chamber; and
   wherein the second gas supply comprises an air pump and feedback from the pressure sensor is used to control the air pump.

16. Apparatus according to claim 1 further comprising:
   an air pump;
   an air supply line connecting the air pump to the delivery line;
   one or more valves in the air supply line;
   and a control system configured to generate one or more outputs to control the one or more valves;
   wherein the control system has a low pressure override mode, in which it operates the one or more valves to deliver air from the air pump into the delivery line.

17. Apparatus according to claim 16 further comprising:
   one or more pressure sensors in at least one or the delivery line, supply line or gas reservoir and wherein the control system is configured to receive data from said one or more pressure sensors and generate one or more outputs to control one or more valves in the apparatus.

18. An apparatus for delivering a gas to a patient's body, the apparatus comprising an apparatus according to claim 1 which further comprises a medical device suitable for injecting a gas from the gas delivery apparatus to a patient's body.

19. An apparatus according to claim 18, wherein the medical device is a cannula for insertion into a patient's eye.

20. Apparatus for gas delivery, comprising:
- a gas reservoir comprising a cylindrical chamber and a piston, the cylindrical chamber comprising a first region defined by a first end of the chamber and a first face of the piston and a second region defined by a second end of the chamber and a second face of the piston;
- a delivery line between the first region of the gas reservoir and a fluid outlet;
- a first supply line between a first gas supply inlet connectable to a first gas supply and the first region of the gas reservoir;
- a second supply line between a second gas supply inlet connectable to a second gas supply and the first region of the gas reservoir; and
- a pressure control line with an inlet connectable to a second gas supply, the pressure control line being coupled to the opening of the second region of the gas reservoir to thereby control the pressure in the gas reservoir.

* * * * *

UNITED STATES PATENT AND TRADEMARK OFFICE
CERTIFICATE OF CORRECTION

| | | |
|---|---|---|
| PATENT NO. | : 9,072,847 B2 | Page 1 of 1 |
| APPLICATION NO. | : 13/129783 | |
| DATED | : July 7, 2015 | |
| INVENTOR(S) | : Nicholas Evans and Kenneth Smith | |

It is certified that error appears in the above-identified patent and that said Letters Patent is hereby corrected as shown below:

Title page, (87) replace the date of "May 7, 2010" in the PCT Pub. Date with -- May 27, 2010 --.

Signed and Sealed this
Seventeenth Day of November, 2015

Michelle K. Lee
*Director of the United States Patent and Trademark Office*